United States Patent [19]
Farrell

[11] Patent Number: 5,259,762
[45] Date of Patent: Nov. 9, 1993

[54] ORAL APPLIANCE

[76] Inventor: Christopher J. Farrell, Ste. 1, Ferry Road Plz., CNR. Ferry Rd. & Drury Ave., Southport Queensland 4215, Australia

[21] Appl. No.: 838,198
[22] PCT Filed: Sep. 6, 1990
[86] PCT No.: PCT/AU90/00399
  § 371 Date: Mar. 6, 1992
  § 102(e) Date: Mar. 6, 1992
[87] PCT Pub. No.: WO91/03215
  PCT Pub. Date: Mar. 21, 1991

[30] Foreign Application Priority Data
  Sep. 6, 1989 [AU] Australia .................. PJ 6190

[51] Int. Cl.⁵ .................................. A61C 5/00
[52] U.S. Cl. .................................. 433/215; 433/6
[58] Field of Search .......................... 433/6, 215

[56] References Cited
U.S. PATENT DOCUMENTS

| | | | |
|---|---|---|---|
| 4,568,280 | 2/1986 | Ahlin | 433/6 |
| 4,810,192 | 3/1989 | Williams | 433/6 |
| 4,920,984 | 5/1990 | Furumichi et al. | 433/6 |
| 4,986,751 | 1/1991 | Bergersen | 433/6 |
| 5,163,840 | 11/1992 | Bourke | 433/6 |

Primary Examiner—John J. Wilson
Attorney, Agent, or Firm—Kimmel, Crowell & Weaver

[57] ABSTRACT

An oral appliance for repositioning the temporomandibular joint includes a base portion having a generally U-shaped form to follow the jaw and teeth of a user and front and rear flanges which define with the base portion upper and lower channels for receiving the teeth of the upper and lower jaws. The base portion is of asymmetrical form on either side of the appliance from the leading to the trailing end thereof so as to substantially occupy uneven spacing between the upper and lower jaws of the user and cause the lower jaw to move into substantial alignment with the upper jaw.

11 Claims, 8 Drawing Sheets

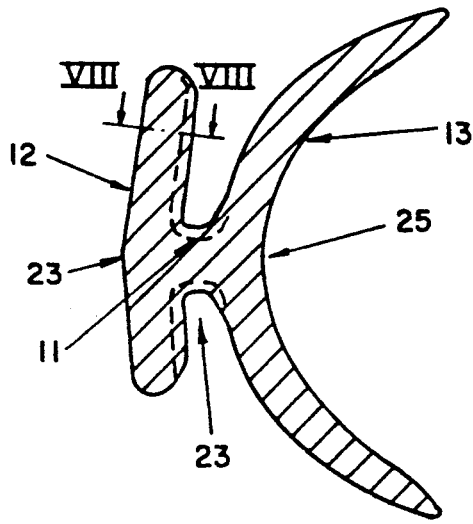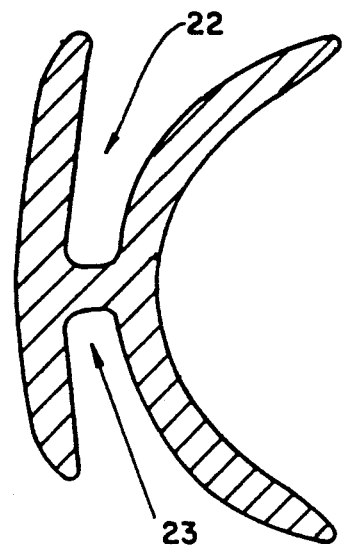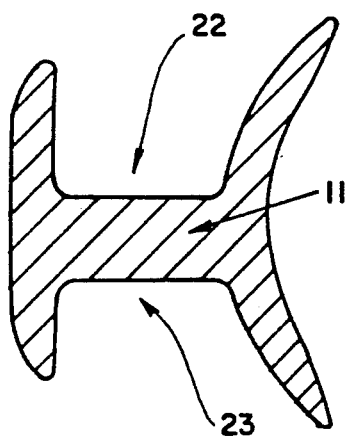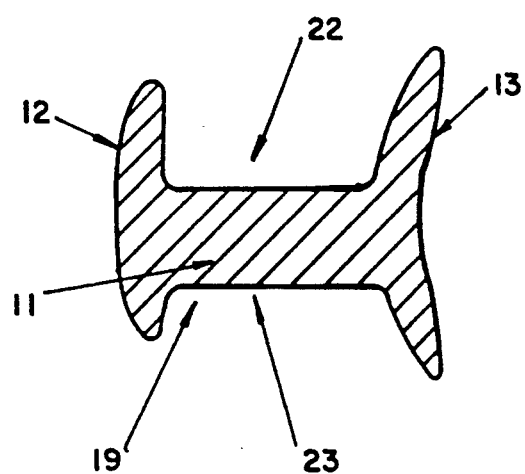
FIG. 12
FIG. 5
FIG. 6
FIG. 7
FIG. 8

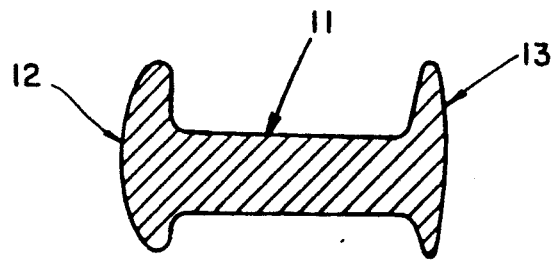
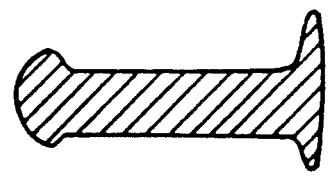
FIG. 9     FIG. 10
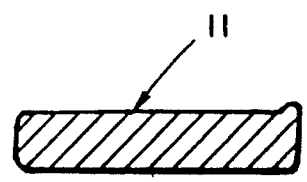
FIG. 11
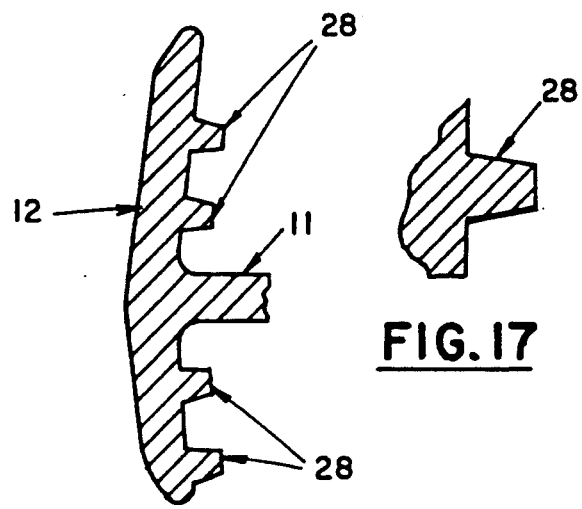
FIG. 16     FIG. 17     FIG. 18

ORAL APPLIANCE

FIELD OF THE INVENTION

This invention relates to an oral appliance and in particular to an orthopedic repositioning appliance.

DESCRIPTION OF THE PRIOR ART

Headache and jaw problems are often associated with incorrect harmony of the muscles and nerves of the jaw, skull and neck mechanism, an area called the Cranio-Mandibular System. A part of this system is the temporomandibular joint (TMJ) which comprises the joint which connects the lower jaw or mandible to the skull with temporal muscles in the region of the joint suspending the mandible from the skull. These muscles are used inter alia for speaking, swallowing eating and breathing and permit the mandible to be open and closed and moved forwardly and to the rear.

In a perfect bite with correct dental occlusion, the teeth of the upper and lower jaws come together. Misalignment of the upper and lower jaws however is a common occurrence caused by lack of development of the lower jaw resulting in a deep bite curve between the teeth of the upper and lower jaws. Misalignment of the joint caused by structural imbalances or other reasons can also cause a number of problems including headache, neck tension, curvature of the spine, muscular weakness and poor coordination. Furthermore, it has been found that a person loses strength when the joint is out of alignment. When the joint is under stress due to imbalance, the body uses up muscular strength causing fatigue and pain. In the case of athletes, misalignment of the joint results in decreased performance.

It has been found that by aligning the TMJ, dramatic improvements in athletic capabilities occur, in particular strength. Custom fitted plastic bite plates known as mandibular orthopedic repositioning appliances (MORA) have been proposed to relax the temporal muscles so as to permit the muscles to rest from their constant strain and thus relieve headaches and neck tension and in the case of athletes, to improve athletic performances. Such appliances however are required to be custom fitted to the user by taking impressions from the jaw and subsequently moulding the bite place. Such appliances have proved to be relatively expensive and of limited applicability.

Other oral devices are also used for a number of other purposes. For example, mouthguards are commonly used in sporting applications to protect the teeth of a user against damage. Such mouthguards range from inexpensive (and relatively inefficient) devices which the user shapes his- or herself to the form of the jaws or teeth to the more expensive devices fitted by dentists or orthodontists. In each case, the known mouthguards are intended only for protection purposes and have, and are intended to have, no other function.

There is also known in the art an oral appliance which is used primarily for teeth cleaning purposes. Such an appliance is in the general form of a mouthguard but is formed of relatively flexible material and is provided with a plurality of projections which serve when the appliance is worn to remove food particles from between the teeth. Such an appliance is only used on a short term basis for cleaning and again has no other purpose.

Another form of mouth appliance which is well known is the dummy which may be of many different forms and which is primarily used to pacify babies and young children. Generally however dummies can have a detrimental affect on teeth formation and positioning.

SUMMARY OF THE INVENTION

The present invention aims to provide an oral appliance which has the effect of repositioning the TMJ joint and which may be simply and easily used by a user. The present invention aims to provide an oral appliance which is relatively inexpensive. The present invention may be embodied in a number of difference appliances and in one preferred aspect in an appliance which is suitable for the prevention of orthodontic problems in growing children and for assisting in the correction of development anomalies.

The present invention in a further aspect is embodied in an oral appliance which may be used for the relief of the symptoms of muscle tension headaches. In yet a further aspect, the present invention is embodied in an oral appliance suitable for improving performance in particular sports. The present invention in a yet a further aspect is embodied in an oral appliance suitable for use as a children's dummy or pacifier. Other objects and advantages of the invention will become apparent from the following description.

With the above and other objects in view, the present invention provides an oral appliance adapted for repositioning the temporomandibular joint, said appliance including a base portion shaped so as to be located between the teeth of the upper and lower jaws of a user, and outer and inner flange portions along the leading and trailing edges of said base portion and extending to opposite sides thereof so as to form upper and lower channels for accepting the teeth of the upper and lower jaws and wherein said base portion has a cross sectional form adapted to substantially occupy space between said teeth of said upper and lower jaws so as to provide a support for the jaws of the user.

The present invention also provides a method for relieving the symptoms of muscle tension headaches, said method including the steps of placing an appliance of the above type in the mouth of a headache sufferer, closing the teeth on said appliance and maintaining said appliance in the mouth for an extended period of time suitably in the region of one hour. Whilst the method of the present invention is particularly suitable for use with the appliance of the above described type it may also be used with an appliance wherein the base portion has a substantially constant cross-section along its maximum dimension.

Preferably, the base portion is of generally U-shaped plan form and tapers in thickness along the channels on each side of the appliance from regions adjacent the trailing ends of said appliance towards the leading end thereof. Preferably, also, said base portion tapers in thickness from said regions to the trailing ends of said appliance. The base portion is thus designed to substantially occupy the space between the upper and lower jaws resulting from a deep bite curve and put more pressure on the rear molars thereby relaxing and exercising the joints and muscles. Most preferably, the variation in thickness in the base portion is achieved by forming said base portion on opposite sides of the appliance asymmetrically with the top side of the base portion being generally planar or flat. Suitably, the base portion is formed as an asymmetric aerofoil shape with the asymmetric or curved surface thereof being disposed on the operative lower side of said appliance and the maximum depth of the aerofoil being located at a said region on opposite sides of said appliance.

Suitably, the appliance may be provided with a plurality of projections which extend inwardly into the channels to engage the teeth and or gums. The projections may be of tapered form or alternatively, the projections may be headed and the projections are provided on the base portion on opposite sides thereof and/or on the inner surfaces of said outer and/or inner flanges.

When the appliance of the invention is used for sporting or other purposes, it is suitably centrally apertured through the flange portions and/or the base portion so as to facilitate breathing by the user. Alternatively, a series of apertures may be formed through the outer flange portions for this purpose.

When the appliance of the invention is applied for usage as a dummy or pacifier, it is suitably provided with a handle portion which in use is arranged externally of the mouth of a user.

When the base portion is formed as above, the lower jaw of the user is moved downwardly and forwardly so that the jaws of the user are fully supported and that muscles about the jaw are in a relaxed or substantially relaxed state.

The appliance of the invention is suitably formed of a flexible material such as a latex rubber, silicone or PVC material which may readily deflect to fit the mouth of the user.

BRIEF DESCRIPTION OF THE DRAWINGS

In order that the invention may be more readily understood and put into practical effect, reference will now be made to the accompanying drawings which illustrate a preferred embodiment of the invention and wherein:

FIGS. 5 to 11 are sectional views of the appliance along lines I—I, II—II, III—III, IV—IV, V—V, VI—VI and VII—VII respectively of FIG. 4;

FIG. 12 is a sectional view along line VIII—VIII of FIG. 5;

FIG. 16 is a part sectional view at I—I of FIG. 4 of an appliance having bristles;

FIGS. 17 and 18 illustrate in enlarged sectional elevational and plan view the bristles of the appliance of FIG. 16.

DETAILED DESCRIPTION OF THE INVENTION

Figure 1:
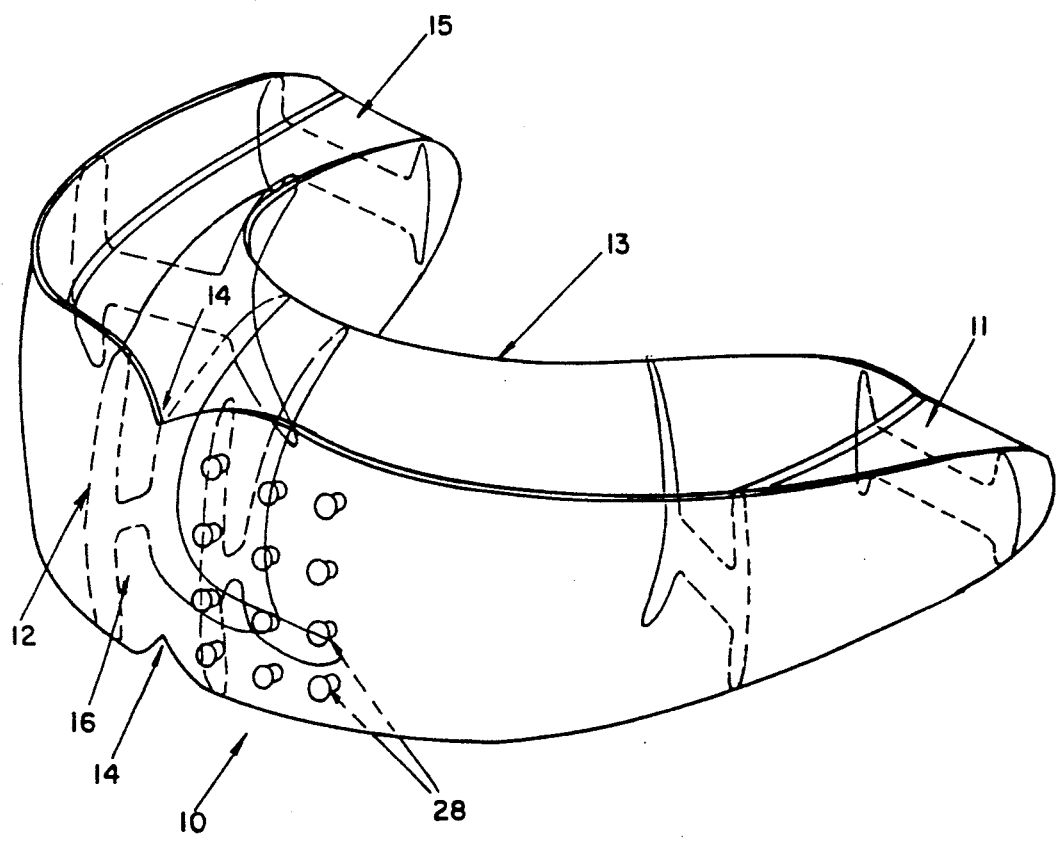
FIG. 1 is a perspective view of one form of oral appliance according to the present invention.

Referring to the drawings and firstly to FIGS. 1 to 4, there is illustrated a first form of oral appliance 10 according to the present invention. The appliance 10 includes a base portion 11 which is of a somewhat arcuate or U-shaped plan form so as to follow substantially the shape of the jaws and teeth pattern of a person. The base portion 11 is provided along its leading edge with an outer flange portion 12 and along its trailing edge with an inner flange portion 13. The flange portions 12 and 13 define with the base portion 11 upper and lower channels 15 and 16 for receipt of the teeth of the upper and lower jaws. The outer and inner flange portions 12 and 13 are shaped to the labial and lingual aspects of the upper and lower jaws whilst at the central leading portion of the appliance 10, upper and lower locating cutouts or notches 14 are provided in the flange portion 12.

Figure 2:
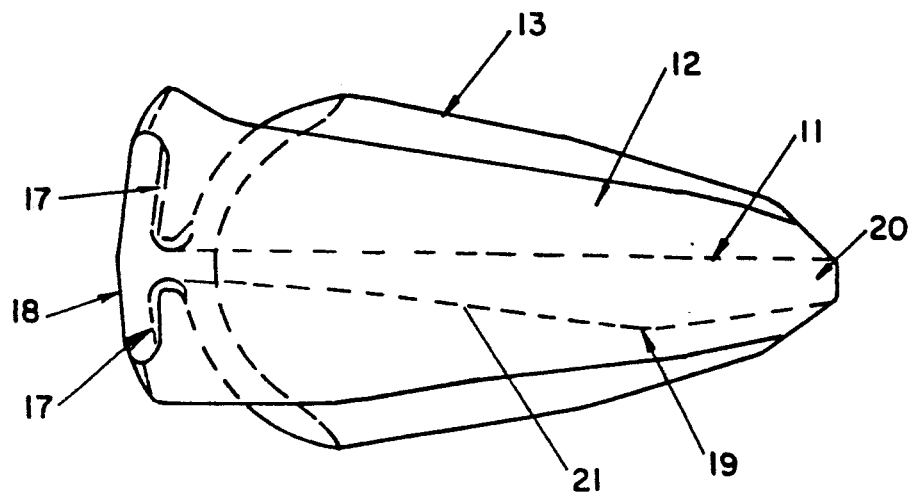
FIG. 2 illustrates in side view the appliance of FIG. 1.

The appliance 10 as shown in FIG. 2 may also include upper and lower ribs 17 which as shown more clearly in FIG. 12 may have a triangular cross section, the ribs 17 being arranged centrally at the leading end of the appliance and extending into the channels 15 and 16. The ribs 17 are provided for positioning the appliance centrally within the mouth of the user for location between the front two teeth of the upper and lower jaw.

Figure 3:
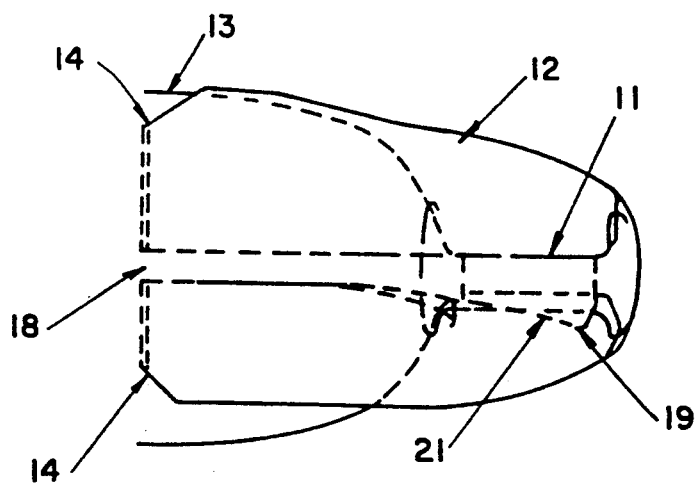
FIG. 3 is a half front elevational view of the appliance of FIG. 1.
Figure 4:
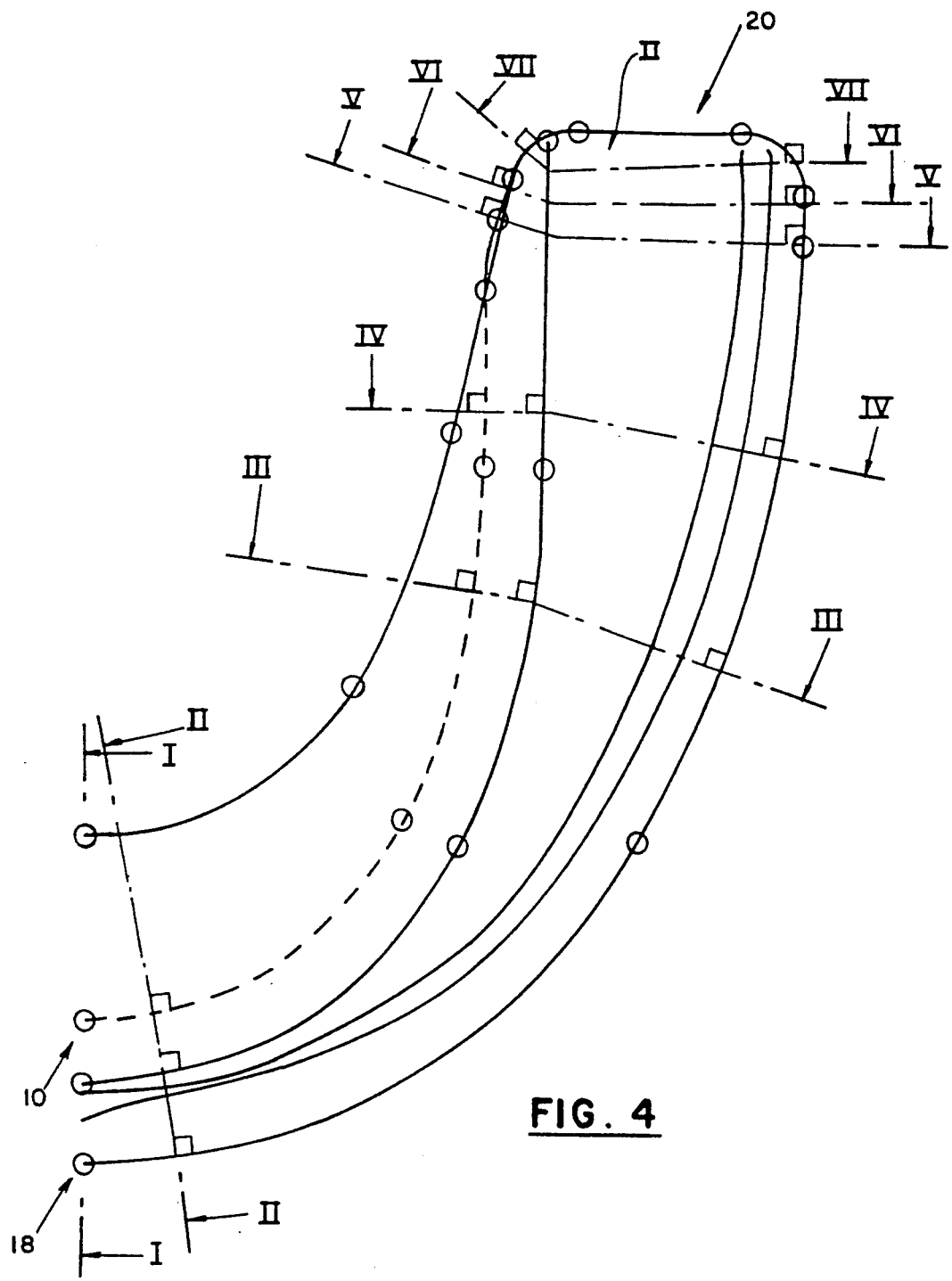
FIG. 4 is a half plan view of the appliance of FIG. 1.

The base portion 11 of the appliance 10 most preferably has a thickness which tapers towards the central leading end 18 of the appliance in the manner shown in FIGS. 2 and 3 from a maximum at regions 19 adjacent the trailing ends 20 of the appliance and then tapers to the trailing ends of the appliance from those regions so as to form a shape of substantially asymmetric aerofoil form with the asymmetric or curved surface 21 of the aerofoil being located on the lower side of the appliance 10. Suitably, the base portion 11 has a thickness of approximately 2 mm. adjacent the leading end 18 of the appliance which increases to a maximum thickness of approximately 4 mm. at the regions 19 towards the trailing ends 20 of the appliance 10 and then reduces to a thickness of approximately 3 mm. at the trailing ends 20.

As shown more clearly in FIGS. 5 to 11, the inner and outer flanges 12 and 13 define the upper and lower channels 22 and 23 for receipt of the teeth of the upper and lower jaws with the channels 22 and 23 for this purpose increasing in width from the central leading end 18 of the appliance 10 to the trailing ends 20 thereof. As is apparent also the flanges 12 and 13 taper in height from the leading end 18 of the appliance 10 to the trailing ends 20 thereof.

The base portion 11 is generally planar or flat on its top side whilst as described above, the base portion 11 increases in thickness from the leading end 18 of the appliance to a maximum at the region shown at FIG. 8 from where it reduces in thickness to the section shown in FIG. 11.

Figure 13:
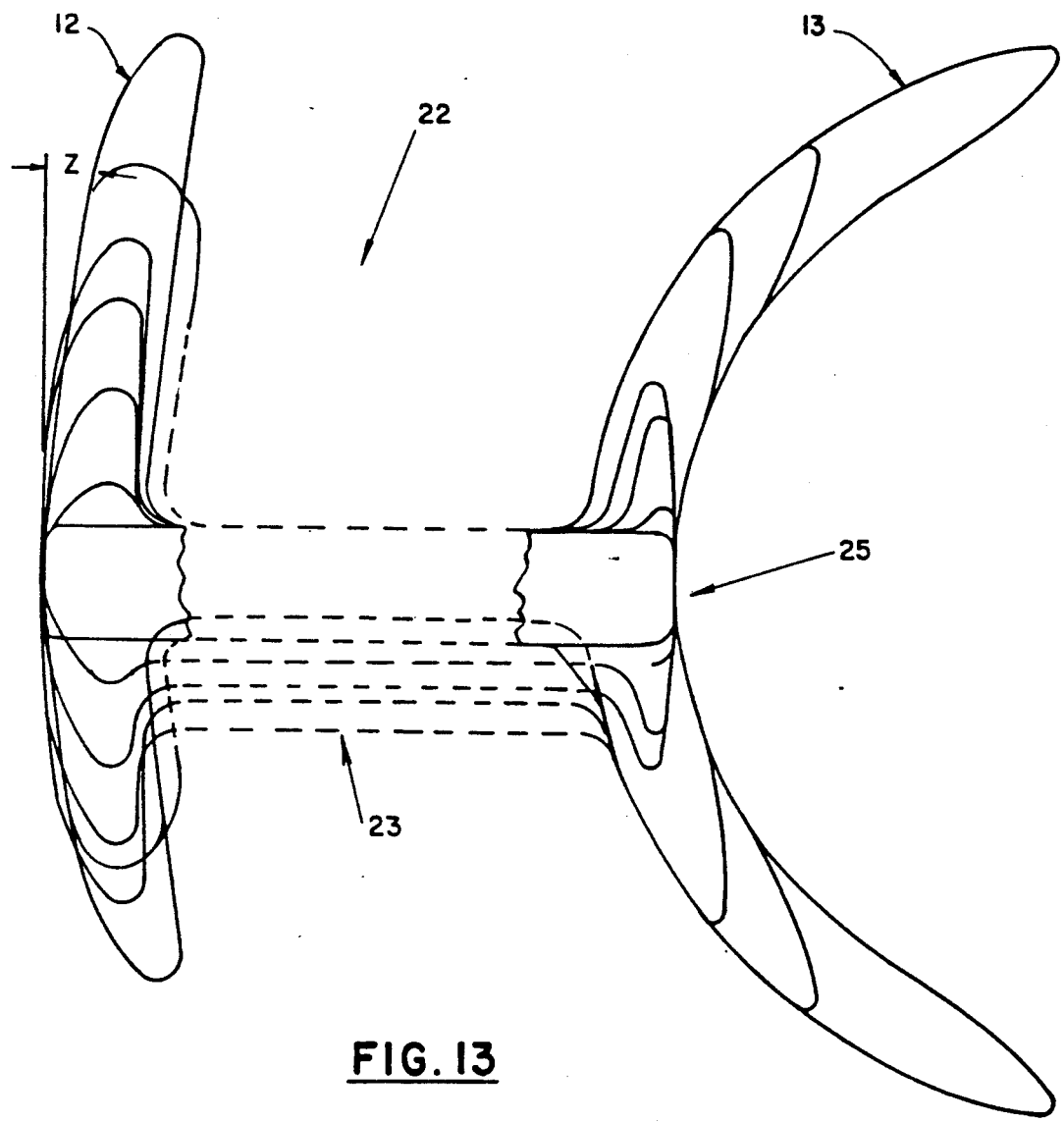
FIG. 13 illustrates the sections of FIGS. 5 to 11 overlaid.

As is more apparent in FIG. 13, the front flange 12 is inclined to the vertical away from the leading end 18 of the appliance 10 on opposite sides of the base portion 11. The angle of inclination of the flange 12 (marked Z in FIG. 13) on the upper side of the base portion 11 decreases from a maximum at a position at the leading end 18 of the appliance (see FIG. 5) to zero towards the trailing end 20 shown at FIG. 9. Suitably the maximum angle of inclination is in the region of 7 degrees. Furthermore, the upper and lower portions of the flange 13 merge into each other at the base portion 11 through a radiused section 24 and the radius of the radiused section decreases to that shown in FIG. 9 after which it increases until the curve flattens to a perpendicular line as shown in FIG. 11.

The trailing flange 13 is of generally arcuate cross section so as to define a rearwardly directed recess 25 for positioning the tongue of the user and so as to improve retention of the device in the oral cavity.

The leading face of the flange 13 preferably stays on the same radius from the leading to the trailing ends of the appliance although the width of the flange 13 reduces as is apparent in FIGS. 9 and 10 approaching the trailing ends of the appliance 10. At the trailing side of the flange 13, the surface of the flange 13 is disposed along the same radius forming a concavity however the width of the flange 13 on either side of the base portion 11 reduces so that the concave curve merges into a convex curve which flattens as shown in FIG. 11 to a perpendicular line at the trailing ends of the apparatus.

Figure 14:
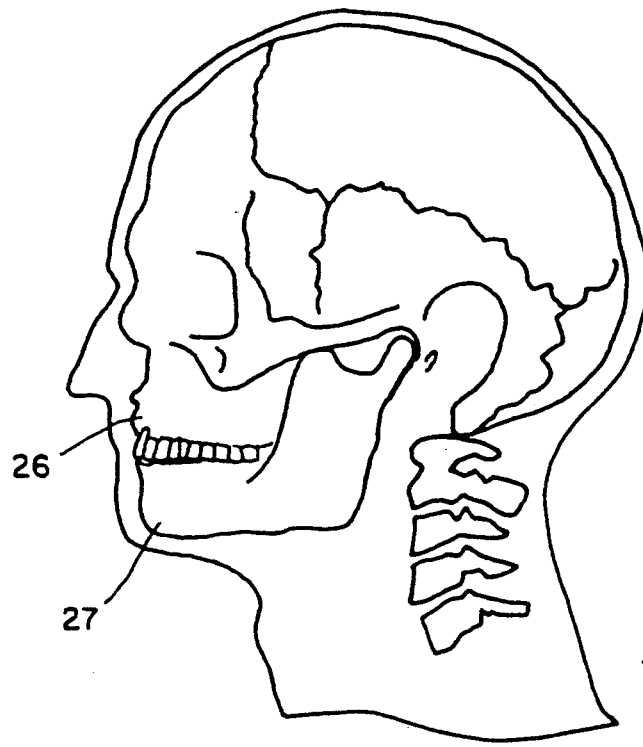
FIG. 14 illustrates schematically a skull and jaw in an unbalanced state.
Figure 15:
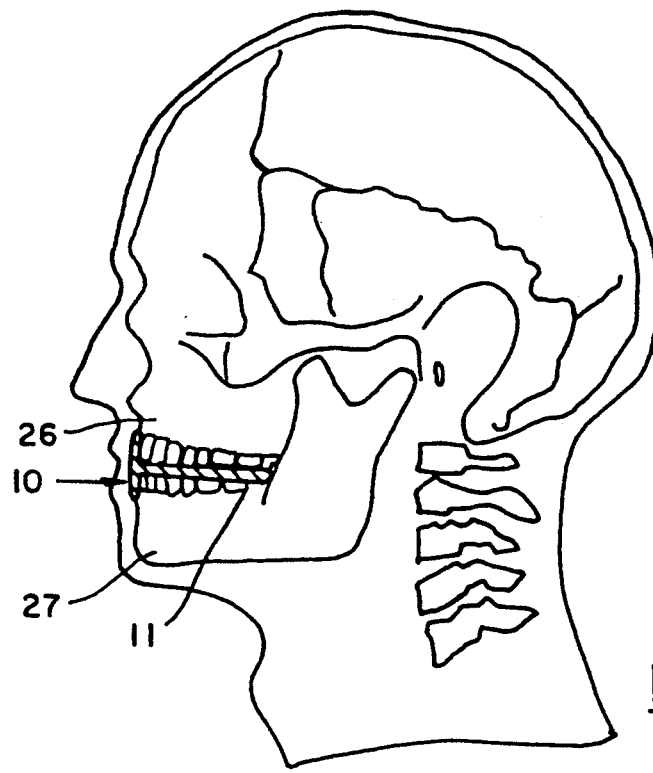
FIG. 15 illustrates the manner in which the oral appliance of FIG. 1 repositions the jaws.

In use, the appliance 10 is applied to the mouth of the user and the effect of the inner and outer flange portions 12 and 13 is to promote relaxation of the muscles controlling the lower jaw so as to also relax the reciprocal muscles of the head and neck. This is further facilitated by the shape of the base portion 11 which supports the lower jaw and encourages the lower jaw to assume its anatomically correct relationship with the upper jaw. Relaxation of the aforesaid muscles in the head and neck will decrease the majority of muscle tension headaches. This will be further apparent from FIGS. 14 and 15 where as shown in FIG. 14, the misaligned upper jaw 26 and lower jaw 27 come together incorrectly with the lower jaw 27 and teeth disposed rearwardly of the upper jaw 26 and teeth in a non-perfect bite situation, this causing muscle overload and also the cervical vertebrae to be incorrectly aligned thus leading to pain in the user.

Where the appliance 10 of the present invention is employed as shown in sectional view in FIG. 15 and when the teeth are closed on the appliance 10 the jaws 26 and 27 are repositioned, the lower jaw 27 moving downwardly and outwardly to the perfect bite position with the teeth in substantial alignment with the teeth of the top jaw 26 so that stretching of the muscles does not occur which accordingly reduces the symptoms of muscle tension headaches.

When used for headache relief or relief of neck pain, the appliance 10 is placed into the mouth and the teeth closed upon the appliance lightly to move the jaws into a more balanced position. It is preferred that a person suffering from headaches sit quietly in a relaxed position for a minimum of one hour, whilst assuring the neck and head are well supported. The appliance may be used as required when headaches are most severe.

For exercising the head and neck muscles and to improve oxygen flow to the face muscles, the appliance 10 may be used actively being gently chewed for 10 minutes. The appliance 10 can also be worn at night whilst sleeping to alleviate teeth-grinding, morning stiffness or morning headaches.

Regular use of the appliance of the invention will serve to reprogram the Cranio-Mandibular area and retrain the muscles into functioning as intended.

Further advantageous properties may be achieved by the incorporation of bristles or projections 28 (see FIGS. 1 and 16) on at least the inner faces of the flange 12 on the upper and lower side of the base portion 11 and suitably in the region of the leading portion thereof. The bristles 28 as shown in FIGS. 17 and 18 are of frustoconical form and arranged in aligned rows. The bristles 28 serve as further locating means for the appliance as well as serving to massage the gums of the user.

Preferably, the appliance is formed of latex rubber, silicon rubber or medical PVC material, however, any other flexible synthetic material may be suitable for forming the appliance.

Figure 19:
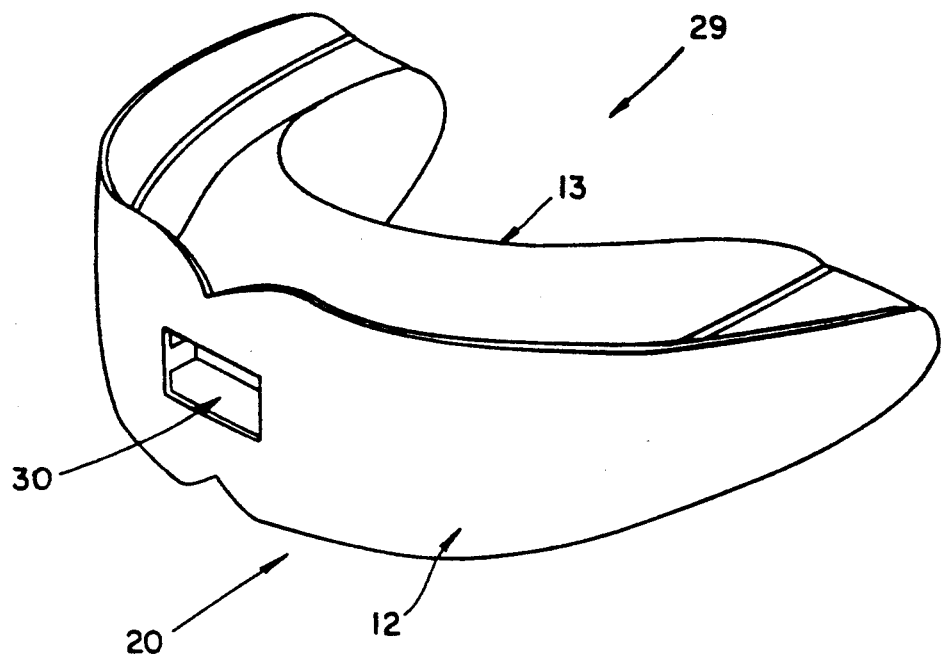
FIGS. 19 and 20 illustrate the application of the appliance of the invention to a sports appliance and dummy respectively.

FIG. 19 illustrates a further embodiment of appliance 29 suited to sports appliance applications. This embodiment is similar to the above described embodiment and accordingly like parts have been given like numerals. In this case however, the base portion 11 has an increased thickness whilst retaining the substantially aerofoil shape with a suitable maximum thickness being up to 9 mm. Furthermore, in this embodiment, the central region of the appliance is apertured through the flange 12 and base portion 11 so as to define a large air breathing hole 30 necessary for sports applications. In this embodiment also, the projections 28 if used may be of 2 or 3 mm length.

This appliance which can be mass produced in several sizes is designed to increase the available strength in athletes by holding the jaws in their optimum strength position. The appliance which suitably is formed of a medicinal PVC may be used in all sports but specifically for golf, tennis, weightlifting and athletics.

Figure 20:
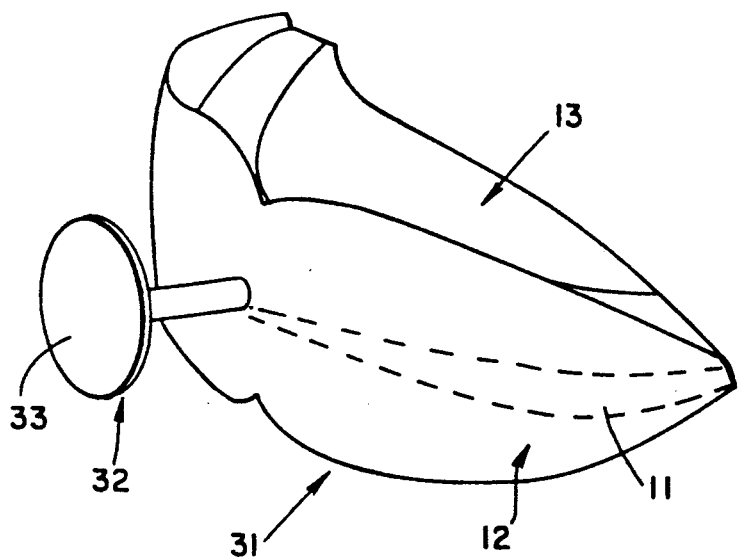

Referring now to FIG. 20 there is illustrated a further embodiment of appliance 31 according to the invention suitably for use as a dummy or pacifier for babies or young children. Again like parts to the previous embodiments have been given like numerals. In this form, the appliance 31 is provided with an integral handle portion 32 which projects outwardly from the central portion of the appliance to be normally located outside the mouth. Preferably, the handle portion 32 includes an enlarged head 33 of any suitable form to facilitate gripping. The handle portion 32 may be formed of hard plastics material and either as stated above be formed integrally with the main body of the appliance 31 or secured thereto in any suitable fashion. It will be apparent in this form that the appliance 31 is considerably smaller in dimensions than the appliance described with reference to FIGS. 1 to 19 so as to suit the size of baby's mouths. As with the other type of appliances, however, this appliance may be made different sizes so as to suit a range of mouth sizes.

The inner and outer flange portions 12 and 13 help pacify children and the shape of the flanges promote correct tongue position and dental eruption. Furthermore, when chewed, the appliance does not have the adverse orthodontic effects of conventional dummies. The projections 28 if used also help with teething problems and stimulate healthy blood flow through the gum tissues.

Whilst the above has been given by way of illustrative embodiment of the invention many variations may be made thereto without departing from the broad scope and ambit of the invention. For example whilst it is preferred that the base portion 11 of the appliance have an aerofoil shape in some situations such as for headache relief the base portion 11 may have a constant cross-section throughout its length. Furthermore, in the embodiments described above the appliances are provided with two rows of projections on the inner and outer flange portions and on the base portion and on the upper and lower sides of the appliance. In some situations more than two rows of projections may be provided or alternatively the projections may be provided in a random array. In other situations the projections may be eliminated.

The appliance of the invention may also be used in combination with toothpaste so as to achieve a beneficial effect on the gums, particularly for those persons suffering from gum disease.

I claim:

1. An oral appliance adapted for repositioning the temporomandibular joint, said appliance including a base portion shaped so as to be locatable in use between the teeth of the upper and lower jaws of a user and leading and trailing flange means along the leading and trailing edges of said base portion and extending to opposite sides thereof so as to form upper and lower channels for accepting the teeth of the upper and lower jaws and wherein said base portion tapers in thickness along said channels on each side of said appliance from regions adjacent the trailing ends of said appliance towards the leading end thereof so as to substantially occupy the space between said teeth of said upper and lower jaws to provide a support for the jaws of the user.

2. An appliance according to claim 1 wherein said base portion further tapers in thickness from said regions to said trailing ends.

3. An oral appliance according to claim 2 wherein said base portion has an asymmetrical longitudinal cross section on opposite sides of said appliance.

4. An oral appliance according to claim 3 wherein said base portion on opposite sides of said appliance has a longitudinal cross section of asymmetric aerofoil shape with the asymmetric or curved surface thereof being disposed on the operative lower side of said appliance and the maximum depth of said aerofoil being located at said region.

5. An oral appliance according to claim 4 wherein the top side of said base portion is generally planar.

6. An oral appliance according to claim 1 and including a plurality of projections which extend inwardly from at least said leading flange means into said channels to engage in use the teeth and or gums of the user.

7. An oral appliance according to claim 6 wherein said projections are of tapered form outwardly of said leading flange.

8. An oral appliance according to claim 1 wherein said flange means is apertured so as to facilitate breathing by the user.

9. A pacifier comprising an oral appliance of the type defined in claim 1 and a handle portion extending outwardly of said appliance from the leading end thereof whereby to be arranged in use externally of the mouth of user.

10. An oral appliance adapted for repositioning the temporomandibular joint of a user having an uneven spacing between the teeth of the upper and lower jaws, said appliance including a generally U-shaped base portion shaped so as to be locatable in use between the teeth of the upper and lower jaws of a user and leading and trailing flange means along the leading and trailing edges of said base portion and extending to opposite sides thereof so as to form upper and lower channels for accepting the teeth of the upper and lower jaws and wherein said base portion tapers in thickness on both sides of said appliance from regions adjacent the trailing ends of said appliance towards the leading end thereof so as to substantially occupy said uneven spacing between said teeth of said upper and lower jaws to provide a support for the jaws of the user and cause said lower jaw to move forwardly and downwardly into alignment with said upper jaw.

11. An oral appliance for repositioning the temporomandibular joint of a user having an uneven spacing between the teeth of the upper and lower jaws, said appliance including a generally U-shaped base portion adapted to be located between the teeth of the upper end lower jaws of said user, said base portion having on opposite sides of said appliance a maximum thickness at regions adjacent trailing ends of the appliance, said base portion tapering in thickness on both sides of said appliance from said regions towards the leading end of said appliance and from said regions towards the trailing ends thereof so as to define a base portion having on opposite sides a longitudinal cross section of a substantially asymmetric aerofoil shape whereby said base portion may substantially occupy said uneven spacing between said teeth of said upper and lower jaws to provide a support for the jaws of the user.

* * * * *